United States Patent [19]
Bjeldbak

[11] Patent Number: 6,039,951
[45] Date of Patent: Mar. 21, 2000

[54] METHOD FOR ATTAINING ERECTION OF THE HUMAN SEXUAL ORGANS

[76] Inventor: Gitte Bjeldbak, Nysumvej 15, Rold, DK-9510 Arden, Denmark

[21] Appl. No.: 09/149,515

[22] Filed: Sep. 8, 1998

Related U.S. Application Data

[63] Continuation-in-part of application No. PCT/DK97/00085, Feb. 27, 1997.

[30] Foreign Application Priority Data

Mar. 11, 1996 [DK] Denmark .................................. 0279/96

[51] Int. Cl.[7] .................................................... A61K 35/78
[52] U.S. Cl. .......................................................... 424/195.1
[58] Field of Search .......................................... 424/195.1

[56] References Cited

U.S. PATENT DOCUMENTS

| | | | |
|---|---|---|---|
| 5,383,848 | 1/1995 | Hillman et al. | 604/20 |
| 5,384,123 | 1/1995 | Metsada | 424/195.1 |
| 5,738,879 | 4/1998 | Rine | 424/70.8 |
| 5,788,982 | 8/1998 | Nadoolman et al. | 424/440 |

OTHER PUBLICATIONS

Choudhary et al., Chem. Br. 33(10): 25–27 (1997). Abstract.
Lazzeri et al., Schandinavian Journal of Urology and Nephrology 28(4): 409–412 (1994).
Kim et al. Journal of Urology 153(2): 361–365 (1995).
Kim et al., Jounal of Urology 141(3): 546–548 (1995).
Owen et al., Journal of Urology 141(3): 546–548 (Mar. 1989).
Segraves et al., Archives of Sexual Behavior 16(2): 125–137 (Apr. 1987).
The Merck Manual of Diagnosis and Therapy, Merck & Co., Rahway, NJ, 1992.
Green, B.G. et al., Chemical Senses, vol. 13(3), p. 367–384, 1988.
Kobayashi, A. et al., Amer. J. of Physiology—Regulatory Integrative & Comparative Physiology, vol. 44(1), p. R92–R98, Jul. 1998.
Rodriguez–Sierra, J.F. et al., Physiology & Behavior, vol. 44, p. 267–272, 1988.
Marieb, E.N., Human Anatomy and Physiology, 2nd Ed., p. 944, 945, and 961, 1992.
Pinter, E. et al., Neuroscience, vol. 68(2), p. 603, 1995.
Lundberg, J.M. et al., Acta Physiol. Scand., vol. 120(2), p. 217–227, Feb. 1984.
Nance, D.M. et al., Brain Research Bulletin, vol. 18(1), p. 109–114, Jan. 1987.

*Primary Examiner*—Jean C. Witz
*Attorney, Agent, or Firm*—Nims, Howes, Collison, Hansen & Lackert

[57] ABSTRACT

A composition for attaining an erection has chili pepper or an extract thereof in a diluted form combined with a lubricant for topical application to human sexual organs.

4 Claims, No Drawings

METHOD FOR ATTAINING ERECTION OF THE HUMAN SEXUAL ORGANS

CROSS-REFERENCE TO RELATED APPLICATION

This application is a continuation in part of International Application PCT/DK97/00085, with an International filing date of Feb. 27, 1997.

BACKGROUND OF THE INVENTION

The present invention relates to a natural product having a sexually stimulating action, intended to be applied in diluted form to a woman's and/or a man's sexual organs.

It is known to use different forms of aphrodisiacs, where the active elements come from plants or other natural products i.e. Myristica fragrans or nutmeg, but these are meant to be taken orally.

If such a product is used, it is necessary to take in the product over a fairly long period of time before the desired effect will appear.

It is also known to use a topical composition containing cayenne pepper for stimulating the blood flow in the skin according to U.S. Pat. No. 5,384,123, where this is used for rejuvenating skin.

Capsaicin, the active component in hot chilli pepper, is known from "Drugs & Aging", 1995, 7 (4), pp 317–328, which discloses a topical composition containing capsaicin with analgesic effect. Analgesics are agents which relieve pain by acting centrally to elevate pain threshold without disturbing consciousness or altering other sensory modalities.

Nevertheless, it is not known to use a topical, pharmaceutical composition containing chilli as an aphrodisiac.

SUMMARY OF THE INVENTION

This invention was developed in view of the foregoing background and to overcome the foregoing drawbacks.

Accordingly, it is an object of this invention to provide a composition which will give a sexually stimulating action within minutes after application.

The aphrodisiac is produced by diluting chilli pepper in some lubricant, which may be e.g. oil, cream or any suitable lubricant. The portions of chilli pepper and diluent are dependent on whether fresh chilli or dried chilli powder is used, and if fresh chilli is used the portion of chilli is dependent on the kind of chilli.

The sexual stimulation is achieved by applying some of the dilution directly on the sexual organs and it gives a sexual stimulating action within 1–120 seconds after application.

DESCRIPTION OF THE INVENTION

While the invention will now be described in connection with a certain preferred embodiment in the following example so that aspects thereof may be more fully understood and appreciated, it is not intended to limit the invention to these particular embodiments. The invention relates to all alternatives, modifications and equivalents as may be included within the scope of the invention as defined by the appended claim. Thus the following examples, which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

A topical composition was prepared from an extract of 1.5 cc pulverised dried extra hot chilli pepper in 100 cc virgin olive oil.

The resulting product was applied to several volunteering women's sexual organs, and 1–120 seconds after application, there was a sexually stimulating action together with an increase of secretion in the vagina. No adverse effects were reported.

EXAMPLE 2

A further topical composition was prepared from an extract of ten whole fresh extra hot chilli peppers in 100 cc virgin olive oil.

The resulting product was applied on the penis of a 83 year old diabetic, who had not had an erection for many years. Within 120 seconds after application he was able to obtain a 60–70% erection as the product also has a sexually stimulating effect on men. No adverse effects were reported.

While the present invention has been disclosed in its preferred embodiments, it is to be understood that the invention is not limited thereto, and may be otherwise embodied within the scope of the following claim.

It will also be realised that the components of the composition of the present invention can be available as dilutions in different concentrations to compensate for the naturally different human sensibility.

What is claimed is:

1. A method for attaining an erection of a human sexual organ comprising applying a composition comprising an effective amount of a chili pepper extract and a carrier selected from the group consisting of lubricants, oils and creams and mixtures thereof topically to the sexual organ.

2. The method of claim 1 wherein the chili pepper extract is obtained from dried pulverized chili peppers.

3. The method of claim 1 wherein the chili pepper extract is obtained from fresh chili peppers.

4. The method of claim 1, wherein the carrier is olive oil.

* * * * *